United States Patent [19]
Fay

[11] 4,356,723
[45] Nov. 2, 1982

[54] PROCESS AND APPARATUS FOR CONTINUOUSLY MEASURING SLUMP

[75] Inventor: Robert W. Fay, Fort Wayne, Ind.

[73] Assignee: Royal W. Sims, Salt Lake City, Utah

[21] Appl. No.: 852,344

[22] Filed: Nov. 17, 1977

Related U.S. Application Data

[63] Continuation of Ser. No. 618,751, Oct. 2, 1975, abandoned, which is a continuation of Ser. No. 218,370, Jan. 17, 1972, abandoned.

[51] Int. Cl.³ .................... G01N 11/00; G01N 33/38
[52] U.S. Cl. ........................................................ 73/54
[58] Field of Search .......................................... 73/54

[56] References Cited

U.S. PATENT DOCUMENTS 1,980,184 11/1934 Butcher ............................ 73/54 X
2,643,542 6/1953 Cronk ................................ 73/54
3,237,437 3/1966 Hilkemeier ....................... 73/54
3,403,546 10/1968 Stratton ............................ 73/54

FOREIGN PATENT DOCUMENTS 128779 8/1959 U.S.S.R. ................................ 73/54

Primary Examiner—Edward R. Kazenske
Assistant Examiner—Joseph W. Roskos

[57] ABSTRACT

The slump of aggregate within a continuously rotatable container is under constant surveillance by measuring the hydraulic pressure within the transmission connecting the motor and the container. Hydraulic pressure at a calibrated continuous speed of the container is correlated to the slump value of the aggregate regardless of the quantity of aggregate within the container so that the aggregate is accurately and continuously measured from the time it is charged to the mixer to the time of on-site discharge. As previously stated, the aggregate is continuously measured both during the time it is charged and at the time of on-site discharge, i.e., during counterrotation of the container.

1 Claim, 4 Drawing Figures

| SLUMP IN INCHES | PRESSURE WITH HYDRAULIC TRANSMISSION CONTROL WIDE OPEN, ENGINE IDLING | PRESSURE WITH HYDRAULIC TRANSMISSION CONTROL WIDE OPEN, ENGINE AT 2000 R.P.M. |
|---|---|---|
| 9 | 725 | 1200 |
| 8 | 800 | 1250 |
| 7 | 875 | 1310 |
| 6 | 950 | 1370 |
| 5 | 1025 | 1425 |
| 4 | 1100 | 1480 |
| 3 | 1175 | 1535 |
| 2 | 1250 | 1590 |
| 1 | 1325 | 1650 |

PROCESS AND APPARATUS FOR CONTINUOUSLY MEASURING SLUMP

This is a continuation-in-whole application of Ser. No. 618,751, filed Oct. 2, 1975 and now abandoned which is a continuation-in-whole application of Ser. No. 218,370 filed Jan. 17, 1972 now abandoned.

BACKGROUND OF THE INVENTION

When aggregate is transported from a mixing plant to a job site it is continuously mixed so that it will remain in a homogeneous unset condition. The mixing occurs within a container referred to as a drum or a bowl by those skilled in the art, the bowl being mounted for rotation on the bed of a self propelled truck. In order to obtain the correct physical properties of aggregate at the point of loading and at the point of discharge, it is necessary to measure the "slump". As previously stated, the aggregate is continuously measured both during the time it is charged and at the time of on-site discharge, i.e., during counterrotation of the container. The "slump" value is a reliable measure of the "set" of the aggregate, its pourability, and spreadability. The slump should be of a certain prescribed value at the time it is poured in order that it will completely fill the form without internal voids and have the desired physical characteristics of pourability, spreadability, etc. at the time of pour. Slump is measured at the time of the pour. During the pour, the drum is counterrotated from the direction in which it normally turns during transport. The slump is continuously measured during both rotation of the drum and counterrotation of the drum. The measurement is continuous in either direction. The direction of rotation of the drum does not have an effect on the measurement of the slump value. If the slump is not of the prescribed value at the building site, it must be adjusted by adding one or a combination of water, cement, gravel, sand. Generally, however, the slump is adjusted by adding water to the mix so that it does have the desired slump.

It is objectionable to make extensive adjustments of the slump at the building site because of delay in time which is expensive both to the transporter of the aggregate and the on site workers who cannot continue with the pour until the slump is the proper value.

It is therefore of substantial importance not only to know the slump at the time the aggregate is charged to the container but also to continuously monitor the slump during the transit time while the bowl is rotating and the internal aggregate is being mixed by the bowl rotation. If the slump does change between the time of charge and the time of pour the driver can determine that a slump change has occurred and what must be done to the aggregate in order to make it suitably adjusted. A tank of water carried on the vehicle and valve controlled by the operator of the vehicle is used to add water to the aggregate to adjust the slump during transit so that the proper slump is attained and an immediate pour can be performed by the operator. In this way, the delay time at the pour site is reduced, making faster deliveries and pours and reducing the down time of the construction workers. The difficulty, however, lies in the different qualities of aggregate and the different quantities of aggregate within the bowl. A slump readout should not be effected by the quantity of charge within the bowl; the slump value of the aggregate charge should be read independently of the amount of aggregate charge. The bowl does not always receive the same charge so that in an 11 yard capacity drum, the slump should read the same value as would the same aggregate in a 5 or 4 or 3 yard charge. It is necessary, therefore, to have a slump readout device which monitors the aggregate regardless of the amount of charge within the bowl. Also, since the mix ratio changes it is necessary to have a slump readout which will provide the necessary slump monitoring regardless of the mix ratio.

In order therefore for an accurate and practical slump monitoring device to be operative, it must be independent of the amount of charge and also it must adequately provide accurate readouts for different mix ratios which are called for. As will be seen in considering the objects of the invention both of these factors are adequately provided for in the present invention.

OBJECTS OF THE INVENTION

The principal object of the present invention is to provide a means for continuously monitoring the slump of an aggregate within a rotatable drum regardless of the quantity of such aggregate.

Another object of the present invention is to provide a continuous method and apparatus for monitoring the slump of an aggregate so that the slump is more accurately and precisely controlled at the point of charge and discharge in order to minimize the delivery time and on-site pouring time.

Another object of the present invention is to provide a continuous method and apparatus for monitoring slump of an aggregate whereby the slump values are accurately calibrated to the particular ratio of mix of aggregate.

Another object of the present invention is to provide a self propelled concrete mixer truck in which aggregate is continuously mixed within a rotatable bowl mounted on the bed of the vehicle and in which the bowl is rotated at a prescribed speed and the hydraulic transmission pressure for effecting rotating force is continuously monitored and related to slump of the aggregate which is rotated within the bowl.

Another object of the present invention is to relate the transmission hydraulic pressure used for rotating the bowl at a calibrated rotational speed of the bowl, and the ratio of the mix, so that the slump can be continuously monitored at the time of loading, during transport, and discharge at the construction site.

Other objects and features of the present invention will become apparent from a consideration of the following description which proceeds with reference to the accompanying drawings.

DRAWINGS

Figures 3, 4:
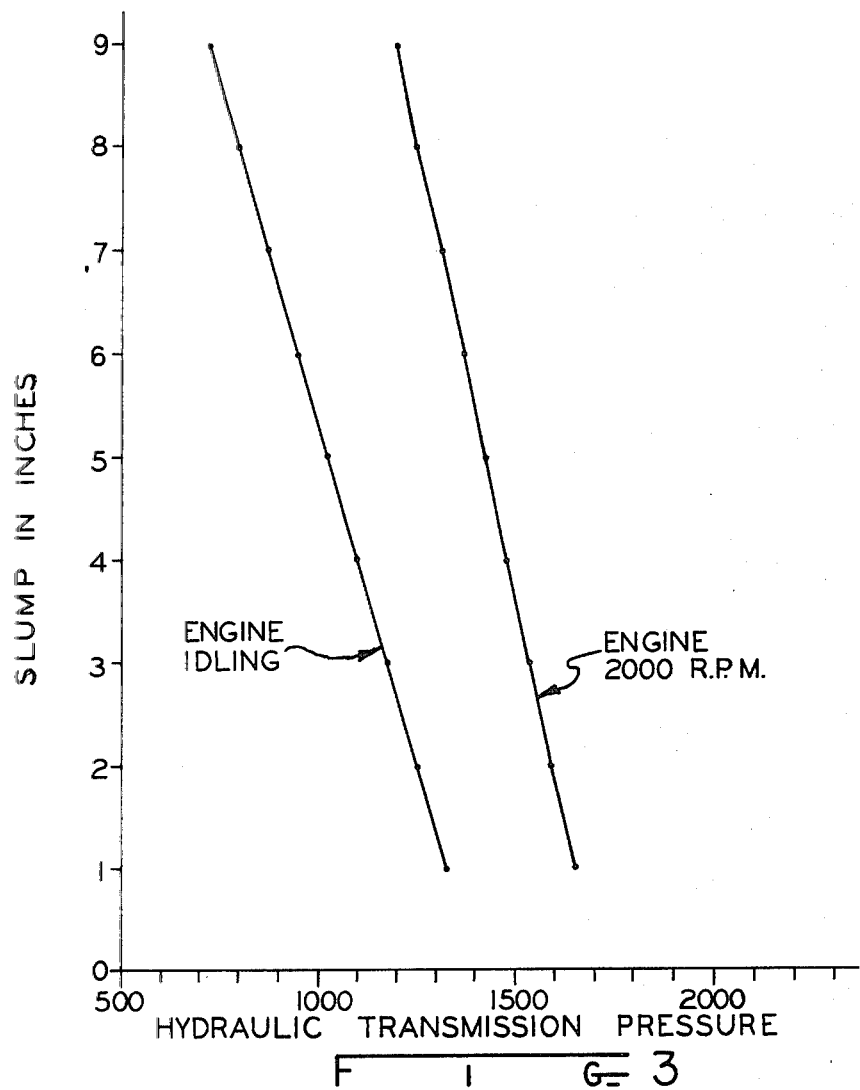

FIG. 3 is a graph correlating slump and hydraulic transmission pressure at two speeds of the truck motor for rotating the bowl, one speed being idling speed and the other speed being at 2000 r.p.m.; and FIG. 4 is a chart correlating slump with hydraulic transmission pressure at two different mixing speeds for the truck drive motor, one being at idling speed and the other at 2000 r.p.m., it being understood that in order for the slump reading to be accurate the rotational speed of the bowl must be constant.

DETAILED DESCRIPTION OF THE INVENTION

Figure 1:
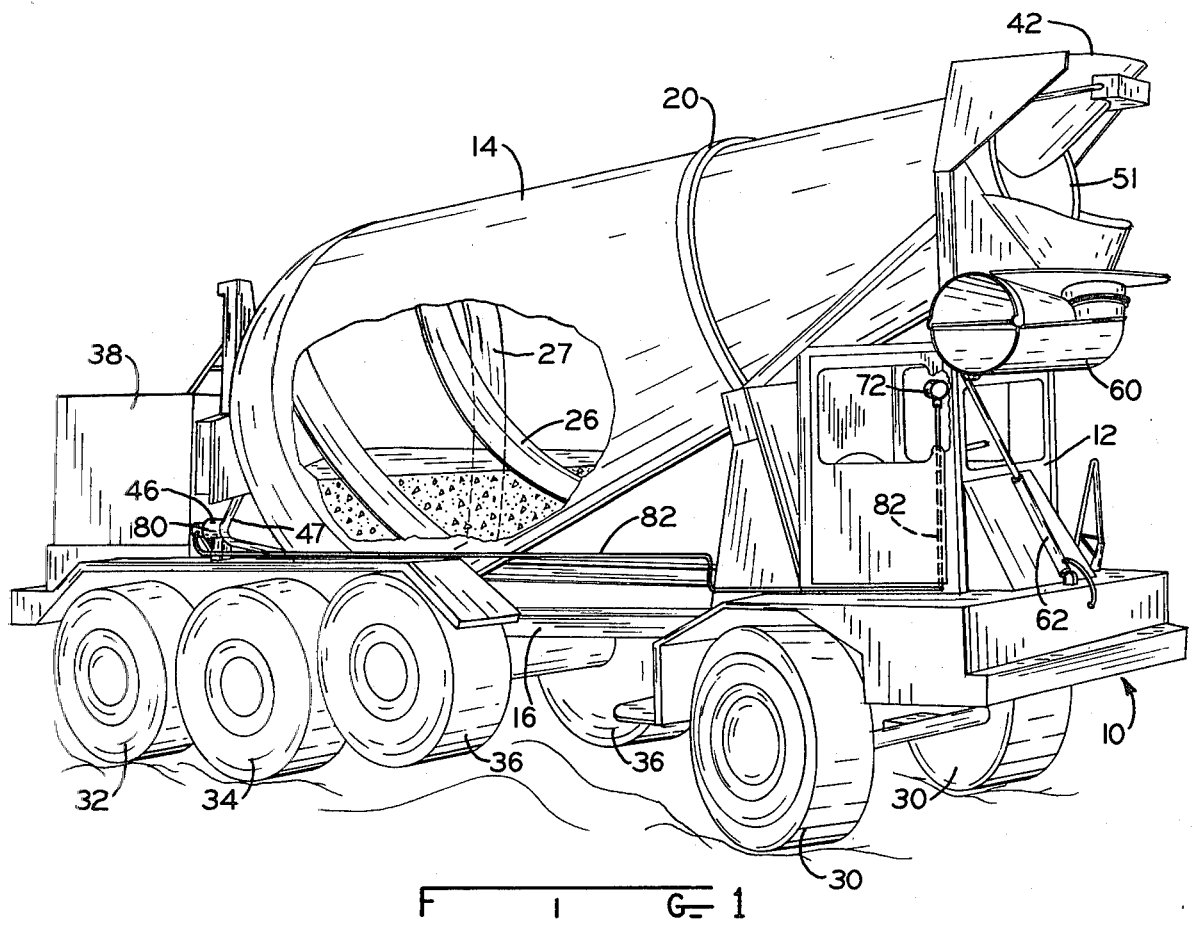
FIG. 1 is an isometric view of a self propelled vehicle having a rotatable mixer bowl for transporting and continuously mixing the aggregate received within the bowl, a portion of the bowl being broken away to show the interior blades or flights therein.
Figure 2:
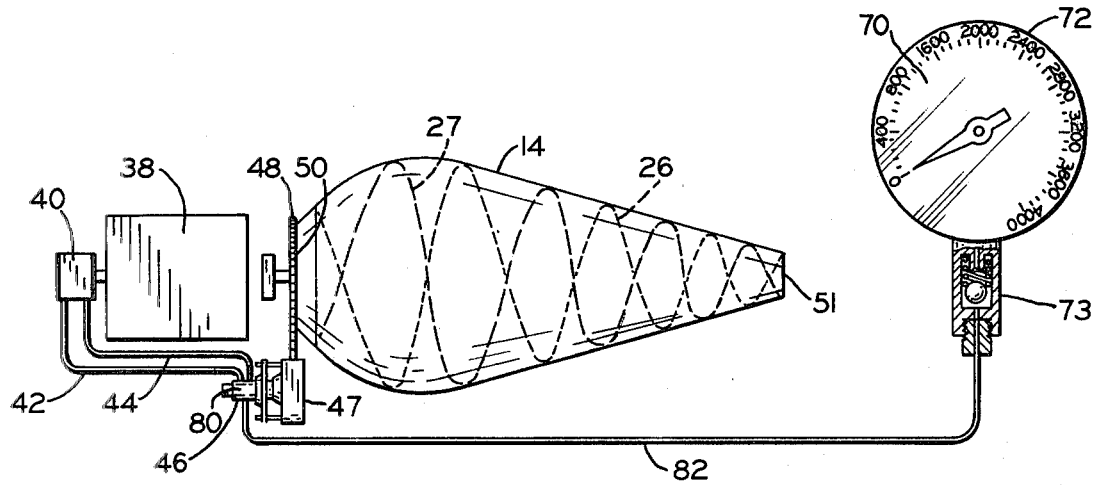
FIG. 2 is a schematic view showing the mixing bowl, motor and hydrastatic transmission connections for effecting rotation of the bowl and the hydraulic tapoff to a gage located within the cab of the truck.

Referring to FIG. 1, a self propelled vehicle designated generally by reference numeral 10 has an operator cab 12 wherein the driver controls both the vehicle and the mixing speed of bowl 14. Bowl 14 is mounted on bed 16 of the vehicle, the general position of the bowl being tipped upwardly at the forward end so the smaller diameter end of the cone shaped article extends over the cab 12. The bowl has a track 20 which is supported on rollers to facilitate turning of the bowl and the interior contains a number of helical blades or flights 26 for mixing the aggregate received within the bowl. The mixing action is continuous so that the aggregate will remain substantially homogeneous and unsettled from the time that it is initially charged to the interior of the bowl until it is discharged during a pour. Mixing action is continuous both during transport and at the time of discharge during a pour since the drum is under continuous rotation in either one direction or the other.

The truck has two steerable front wheels 30 and a series of rear wheels 32, 34, 36 which carry the main load. A separate motor or engine 38 is mounted at the rear of the truck and operates a hydrastatic transmission, one such transmission being obtainable from New York Air Brake and identified as "Dynapower". The transmission consists of a closed loop pump-motor which on the high pressure side develops 4000-5000 psi and on the return line has about 125 psi. The speed and direction of bowl rotations by the transmission is controlled by a swash plate. The details of the transmission are not part of this invention. Hydraulic pump 40 of the transmission has conduit connections 42 and 44 with a hydraulic motor 46 which is connected by means of a planetary reducer 47 and a chain drive 48 connected through a sprocket 50 on the bowl to effect rotation of the bowl 14. It should be noted from FIG. 1, that the blades 26 and 27 are disposed helically in the bowl and extend in parallel directions so that as the drum 14 is rotated in one direction the aggregate or mix contacted by the blade is continuously turned over and tends to remain at the base or large diameter end of the bowl, whereas when the bowl 14 is counterrotated the two sets of helically wound flights 26 and 27 tend to advance the aggregate from the base of the bowl in an upward direction and toward the smaller diameter end 51 of the bowl where it is discharged.

It is the practice, when loading the bowl to drive the vehicle up to a stationary discharge hopper where the aggregate is added in the proper ratio of sand, cement, gravel and water and dropped into chute opening 42 where it is directed to the interior of the bowl. At this time, the bowl 14 is rotating so that the aggregate is continuously mixed from the time it is received within the bowl 14 to the time of discharge, thus, preventing "balling up" of the cement and separation of the ingredients of the aggregate or mixture which thus remains substantially homogeneous. During the time of transit of the vehicle the bowl is continuously rotated by the motor or engine 38 and the speed of mixing is controlled from the cab by the driver through appropriate controls (not shown).

The vehicle has a tank of water (not shown) and by means of a valve the driver can add water during transit as well as during loading and the slump then checked so that at the time the load is ready to be delivered at the building site it is in the proper slump value. The invention has a further value in that during initial charges, the mix has an unknown moisture content and it is very difficult to achieve the correct water content. With the present invention as the charge is made, the gage is read and then water added to achieve the required slump. This charge is then used as the standard for the succeeding loads, thus simplifying successive loads. The operator of the mix plant and the driver co-opt to achieve the desired mix ratio using the gage 72 reading.

After the driver has arrived at the construction site for the pour, the vehicle is maneuvered in full view of the driver and the discharge chute 60 is then extended and disposed horizontally and vertically in the preferred plane by means of a double-acting cylinder (not shown) and extendable piston-cylinder 62 so that the chute is properly located with the pour point at the precise location selected by the driver. The subject matter of the discharge chute including its extensibility and maneuverability is the subject matter of U.S. Pat. No. 3,334,872 "Mechanism for Discharging Concrete" isssued Aug. 8, 1967, and invented by N. S. Hansen et al.

At the time the concrete is discharged, the bowl 14 is counterrotated and both of the sets of blades 27 carry the contents of the bowl vertically upwardly from the base to the discharge opening where it is dropped into the chute 60 and is conducted by the chute to the discharge point at the precise location determined by the chute positioning. During either rotation or counterrotation slump is under continuous measurement and the direction of rotation has no effect on the read-out of hydraulic pressure determinative of the slump. One of the advantages of the present invention is that the discharge point is easily regulated by the driver of the vehicle by maneuvering the vehicle and the chute together, all of this occurring in full view of the driver within the cab 12.

At the time of loading the drum 14 it is necessary to maintain the correct slump which is the measure of the pourability, spreadability and set of the aggregate or mixture. In order to control the slump the ratio of aggregate to water is varied so that the slump will remain relatively constant at the time of charging the drum, during the transit and at the time of pour. The driver can determine whether or not the charge which he has received at the loading station is the correct slump by constantly inspecting the dial 70 of gage 72 which is located within the cab. From the pump 40 to the hydraulic motor 46 is a chamber 80 having a conduit outlet 82 which connects to the gage 72. Referring to FIG. 3, the gage pressure on dial 70 with engine 38 idling, provides a pressure readout so a conversion is then made from the gage pressure to slump readout in inches for engine idle conditions. Of course, there is a different slump readout for each pressure at engine idle and for each different kind of mix. These conversion charts (FIG. 3) are available to the driver in the cab so he can readily convert gage pressure for a given mix into the slump value. If it is desired to provide the slump readout at 2000 r.p.m. output of the engine then the driver with the 2000 r.p.m. engine speed will correlate gage pressure on the appropriate chart (FIG. 3) with the curve labeled "engine 2000 r.p.m." and thereby convert the gage pressure to slump (in inches) to determine if the correct slump has been obtained at the charging station, during the time of transit, and the time of pour.

It should be noted, that by merely regulating the engine speed and by knowing the characteristics of the aggregate it is possible to precisely and continuously monitor the slump by the readout on the face of the gage 70 through a chart (corresponding to the one indicated in FIG. 3) so that either at engine idling or engine 2000 r.p.m., the pressure readout of the gage is directly related to slump in inches. The slump is adjustable either at the loading station or at the pour point by adding water from a tank on the vehicle and the approximate adjustment is made by the driver using a valve for that purpose. More importantly, however, the driver has available to him means for determining whether slump has remained constant and is of the desired value to minimize the down time at the pour point at the site of the construction.

OPERATION

In operation, the driver drives the vehicle to the loading station and receives from the hopper a charge of aggregate in the proper proportion of sand, water, gravel and cement which is poured into the drum or bowl 14 through the inlet chute 42. This mixture is continuously agitated by rotation of the drum 14 in one direction by means of the engine or motor 38 acting through a hydrastatic transmission including a closed loop pump 40, hydraulic lines 42, 44 and hydraulic motor 46. The motor 46 powers a chain 48 and sprocket 50 on the bowl 14 to rotate the bowl 14. When the aggregate enters the drum 14, the drum is rotating at calibrated speed and hydraulic pressure is introduced from chamber 80 through line 82 so the gage 72 within the cab 12 and the pressure reading on the gage for the particular calibrated engine speed is correlated by means of chart (FIG. 3) to read the slump of the aggregate in inches.

From time to time there can be a surge of pressure when the drum starts to rotate or reverses rotation, and there is a check valve 73 within the gage 72 to protect the gage against such surges in pressure.

From the time in which the drum 14 commences to rotate and during the time of transit, while it continues to rotate, the driver maintains a continuous surveillance of the pressure reading on the gage 72 so that he is aware of the slump value. Should the slump not be according to the specification at the loading station, the driver is immediately aware of that fact by the gage reading and makes whatever adjustments are necessary by adding water to provide the necessary slump. During transit, the driver is aware of any changes in slump and can assure the proper slump at the time of pour at the building site.

When the vehicle arrives at the building site the slump is again checked, the unloading chute 60 is extended and adjusted to the angular position so that the pour point is accurately located in full view of the driver in the cab and the drum 14 is then counterrotated so that the helical blades 27 will carry the aggregate from the lower part of the drum upwardly to the smaller diameter end 51 and it will drop into the chute 60 where it is then caused to slide downwardly in the chute and exits at the end of the chute at the proper discharge point. By maneuvering the vehicle and the chute 60 together it is possible to spread the aggregate and facilitate an initial spreading within the form. The advantages of "in-sight" discharge of the aggregate are numerous including avoidance of erroneous discharge, pooling of the aggregate rather than spreading, and it facilitates a rapid and accurate unloading at the proper locations within the form.

Whenever the mix is changed, the operator simply provides the necessary readout graph or chart corresponding with FIG. 3 which correlates the line pressure and slump for a given aggregate at engine idle and engine 2000 r.p.m. output.

Although the present invention has been illustrated and described in connection with a few selected example embodiments, it will be understood that there are illustrative of the invention and are by no means restrictive thereof. It is reasonably to be expected that those skilled in this art can make numerous revisions and adaptations of the invention and it is intended that such revisions and adaptations will be included within the scope of the following claims as equivalents of the invention.

What is claimed is:

1. A process for continuously monitoring the slump of an aggregate while it is unset comprising the steps of: continuously rotating a charge of aggregate within a container having flights therein, coupling the rotatable container to the output drive of a positive drive engine through a closed circuit hydraulic transmission drive having a variable displacement pump and a fixed displacement motor to effect continuous rotation and counterrotation of the container by wobble plate control at a substantially constant speed, communicating during rotation and counterrotation of the bowl the variable hydraulic pressure of the hydraulic transmission through a chamber of said motor to a gage to provide a gage output reading of the pressure, and correlating the variable gage pressure to the slump of a fixed aggregate load at calibrated engine speeds whereby the hydraulic pressures of said motor can be directly related to slump at calibrated engine speeds during rotation or counterrotation of said container, the steps of continuously monitoring slump independently of the direction of rotation of said container, and adjusting the slump to a prescribed value by adjusting the liquid content of said aggregate.

* * * * *